(12) United States Patent
Capps

(10) Patent No.: US 8,741,954 B2
(45) Date of Patent: Jun. 3, 2014

(54) SYNERGISTIC ENHANCEMENT OF CALCIUM PROPIONATE

(75) Inventor: Charles L. Capps, Little Rock, AR (US)

(73) Assignee: ViraTox, L.L.C., Little Rock, AR (US)

( * ) Notice: Subject to any disclaimer, the term of this patent is extended or adjusted under 35 U.S.C. 154(b) by 361 days.

(21) Appl. No.: 12/527,878

(22) PCT Filed: Feb. 21, 2008

(86) PCT No.: PCT/US2008/002299
§ 371 (c)(1),
(2), (4) Date: Dec. 10, 2009

(87) PCT Pub. No.: WO2008/103416
PCT Pub. Date: Aug. 28, 2008

(65) Prior Publication Data
US 2010/0144877 A1    Jun. 10, 2010

Related U.S. Application Data

(60) Provisional application No. 60/902,539, filed on Feb. 21, 2007.

(51) Int. Cl.
*A61K 31/19* (2006.01)
(52) U.S. Cl.
USPC ........... 514/557; 427/384; 427/421; 427/429; 427/428.01
(58) Field of Classification Search
None
See application file for complete search history.

(56) References Cited

U.S. PATENT DOCUMENTS

| | | |
|---|---|---|
| 967,688 A | 8/1910 | Titterley |
| 2,688,586 A | 9/1950 | Eberl et al. |
| 3,046,196 A | 7/1962 | de Vaulchier |
| 3,141,821 A | 7/1964 | Compeau |
| 3,317,376 A | 5/1967 | Schattner |
| 3,650,964 A | 3/1972 | Sedliar |
| 3,658,969 A | 4/1972 | Vaille |
| 3,818,103 A | 6/1974 | von Esch et al. |
| 4,020,183 A | 4/1977 | Asculai et al. |
| 4,045,364 A | 8/1977 | Richter |
| 4,147,803 A | 4/1979 | Asculai et al. |
| 4,390,539 A | 6/1983 | Sherrill |
| 4,499,154 A | 2/1985 | James et al. |
| 4,507,281 A | 3/1985 | Asculai et al. |
| 4,523,589 A | 6/1985 | Krauser |
| 4,659,561 A | 4/1987 | Fives-Taylor et al. |
| 4,737,307 A | 4/1988 | Brown et al. |
| 4,800,235 A * | 1/1989 | La Marre et al. ............ 514/643 |
| 4,822,605 A | 4/1989 | Powell |
| 4,895,452 A | 1/1990 | Yioumes et al. |
| 4,957,734 A | 9/1990 | Miller |
| 5,039,688 A | 8/1991 | Lewis |
| 5,103,497 A | 4/1992 | Hicks |
| 5,108,660 A | 4/1992 | Michael |
| 5,188,822 A | 2/1993 | Viccaro et al. |
| 5,368,837 A | 11/1994 | Baker et al. |
| 5,407,919 A * | 4/1995 | Brode et al. .................... 514/57 |
| 5,456,745 A | 10/1995 | Roreger et al. |
| 5,466,463 A | 11/1995 | Ford |
| 5,510,104 A | 4/1996 | Allen |
| 5,547,677 A | 8/1996 | Wright |
| 5,549,901 A | 8/1996 | Wright |
| 5,560,906 A | 10/1996 | Scodari et al. |
| 5,618,840 A | 4/1997 | Wright |
| 5,662,957 A | 9/1997 | Wright |
| 5,700,679 A | 12/1997 | Wright |
| 5,707,610 A | 1/1998 | Ibsen et al. |
| 5,709,879 A | 1/1998 | Barchfeld et al. |
| 5,747,058 A | 5/1998 | Tipton et al. |
| 5,785,988 A | 7/1998 | Fust |
| 5,855,872 A | 1/1999 | Libin |
| 5,951,988 A | 9/1999 | Little-van den Hurk et al. |
| 5,961,970 A | 10/1999 | Lowell et al. |
| 6,015,832 A | 1/2000 | Baker, Jr. et al. |
| 6,083,525 A | 7/2000 | Fust |
| 6,121,315 A | 9/2000 | Nair et al. |
| 6,235,267 B1 | 5/2001 | Delli Sante et al. |
| 6,245,321 B1 | 6/2001 | Nelson et al. |
| 6,261,540 B1 | 7/2001 | Nelson |
| 6,344,210 B2 | 2/2002 | Fust |
| 6,344,218 B1 | 2/2002 | Dodd et al. |
| 6,348,187 B1 | 2/2002 | Pan et al. |
| 6,361,787 B1 | 3/2002 | Shaheen et al. |
| 6,410,599 B1 | 6/2002 | Johnson |
| 6,423,750 B1 | 7/2002 | Johnson |
| 6,506,803 B1 | 1/2003 | Baker, Jr. et al. |
| 6,559,189 B2 | 5/2003 | Baker, Jr. et al. |

(Continued)

FOREIGN PATENT DOCUMENTS

| | | |
|---|---|---|
| DE | 1105549 | 4/1961 |
| DE | 2312280 | 9/1974 |

(Continued)

OTHER PUBLICATIONS

Cuenca-Estrella, Journal of Antimicrobial Chemotherapy, 2004, 54, 854-869.*
Bradshaw, et al. "Effect of nonionic surfactant on bactericidal activity of cetylpyridinium chloride," J. Pharm. Sci. 61:1163-1164, 1972.
Eckhoff, et al. "Viricidal Efficacy of Mouth and Throat Antiseptics in Suspension Assay," Hyg. Med. 11:324-326, 1986.
International Search Report, International Patent Application No. PCT/US2008/002299, Jun. 2, 2008.
Lewis, "Method of Preventing AIDS Transmission Resulting from Blood Transfusions," Transfus. Sci. 13:11, 1992.

(Continued)

*Primary Examiner* — Wu-Cheng Winston Shen
*Assistant Examiner* — Jean Cornet
(74) *Attorney, Agent, or Firm* — Vinson & Elkins LLP

(57) ABSTRACT

A novel composition comprised of a monocarboxylic fatty acid synergistically enhanced with a dual quaternary ammonium compound to provide immediate fungal and sporicidal destruction with long term residual resistance.

12 Claims, No Drawings

(56) References Cited

U.S. PATENT DOCUMENTS

| | | |
|---|---|---|
| 6,635,676 B2 | 10/2003 | Baker, Jr. et al. |
| 2001/0037100 A1 | 11/2001 | Shanklin |
| 2002/0022660 A1 | 2/2002 | Jampani et al. |
| 2002/0086039 A1 | 7/2002 | Lee et al. |
| 2002/0151521 A1 | 10/2002 | Burke et al. |
| 2004/0043041 A1 | 3/2004 | Baker, Jr. et al. |
| 2004/0101506 A1 | 5/2004 | Fust |
| 2004/0219227 A1 | 11/2004 | Modak et al. |
| 2005/0013836 A1 | 1/2005 | Raad |
| 2005/0065308 A1* | 3/2005 | Markham et al. ............... 528/3 |
| 2005/0169852 A1 | 8/2005 | Roberge et al. |
| 2006/0217286 A1 | 9/2006 | Geoffroy et al. |
| 2006/0252849 A1* | 11/2006 | Rose et al. .................. 523/122 |

FOREIGN PATENT DOCUMENTS

| | | |
|---|---|---|
| DE | 2429033 A1 | 1/1976 |
| DE | 19823319 A1 | 12/1999 |
| EP | 0008121 A1 | 2/1980 |
| EP | 0338515 A1 | 10/1989 |
| EP | 0355536 A2 | 2/1990 |
| GB | 1577926 | 10/1980 |
| WO | WO 99/61045 A1 | 12/1999 |
| WO | WO 2004/019682 A1 | 3/2004 |

OTHER PUBLICATIONS

Zeelie and McCarthy, Analyst 123:503-507, 1998.

* cited by examiner

SYNERGISTIC ENHANCEMENT OF CALCIUM PROPIONATE

This application is a national stage application under 35 U.S.C. §371 of co-pending International Patent Application Number PCT/US2008/002299, filed Feb. 21, 2008, which claims the benefit of U.S. Provisional Patent Application Ser. No. 60/902,539, filed Feb. 21, 2007, each of which are hereby incorporated by reference in their entirety, as if set forth below.

FIELD OF THE INVENTION

The present invention relates to the use of propionic acid and salts thereof as a fungicide for surface contact disinfection and as an additive, coating, or film-forming agent in industrial processes and products where fungicidal properties are desired. The present invention further relates to the solubilization of propionic acid and salts thereof with a dual cationic surfactant in aqueous solution in low concentrations to provide destruction of fungi and their spores in a relative short period of time with subsequent residual toxicity to said fungi and their spores. Furthermore, the present invention provides for the use of a dry powder composition containing propionic acid (and/or a salt thereof) to be incorporated into a solution for use in surface disinfection. The compositions of the present invention allow for disinfection to occur in a relatively short period of time and for an extended residual toxicity.

BACKGROUND OF THE INVENTION

Biological controls for microbials are diminishing as societies construct more confined dwelling spaces. Fungi are one of the most prevalent life forms in nature and are a highly competitive and hardy species. Recent climatic events, such as torrential storms and flooding, have caused severe fungal emergencies that pose risks for human health in many parts of the world. Additionally, construction materials such as wood and paper are ideal food sources for various fungi, some of which are extremely hazardous to human health and may be primary carriers of fungal growths.

Fungicidal action typically occurs as an inhibition of spore germination and/or inhibition of fungus growth. Physiologically, fungicides are normally metabolic inhibitors of electron transport chains, enzymes, nucleic acid metabolism, or protein synthesis, or inhibitors of sterol synthesis. Most of the fungicidal chemicals acting through such modes of toxicity have negative effects on human health, unlike propionic acid and its salts. Therefore, there is a need for an effective fungicide posing low human health risks with immediate and residual toxicity to fungi where infestations may occur.

Propionic acid and its salts are used as a food additive to inhibit microbial growth in breads, cheeses, confections, doughs, puddings, jams and jellies, fresh dough, and meat products. As a food additive, propionic acid and propionic acid salts are designated as generally recognized as safe, or GRAS, by the FDA. Propionic acid has also been used as an antimicrobial inhibitor and preservative in pharmaceuticals, tobacco, cosmetics, animal feeds, and harvested grains and seeds.

Propionic acid occurs naturally in animals (including humans) and dairy products. In animals it is a normal intermediary metabolite that is metabolized to glucose, carbohydrates, amino acids, and lipids, in the same manner as fatty acids (see http://www.nysaes.cornell.edu/fst/fvc/Venture/venture3_chemical.html). Chemically, propionic acid and its salts have a monobasic carboxylic acid structure and its mode of inhibition action on microbials is reportedly due to blockage of acetate in the acetokinase systems, interference with B-alanine in pantothenic acid synthesis, and blockage of pyruvate conversion to acetyl-coenzyme A (Bassler, Anthony: Am J Gastroenterol. 1959 December; 32: 757-70). Medicinally, propionate compounds are typically used as either internal or topical antifungal agents (American Hospital Formulary Service. Volumes I and II. Washington, D.C.: American Society of Hospital Pharmacists, to 1984, p. 84:04).

Historically, the use of propionic acid and its salts as antifungal agents, has had the inherent disadvantage of a relatively short-lived effectiveness. For example, in most food applications the efficacy is reportedly limited to about eight days (Furia, T. E. (Ed.). CRC Handbook of Food Additives. $2^{nd}$ Ed. Cleveland: The Chemical Rubber Co., 1972. p. 139). Despite the short term effectiveness, the low acute and long term health risks coupled with a relatively safe environmental impact makes propionic acid and its salts an attractive ingredient for use as an antifungal inhibitor in some applications. In spite of these attractive qualities, the use of propionate compounds in commercial and industrial applications has been much less common because the concentrations required for acceptable efficacy levels would be considered a human health risk.

Therefore, a need exists for propionate compounds having increased efficacy as a fungicide without increasing human health risks.

SUMMARY OF THE INVENTION

The present invention includes compositions and methods for use in the contact destruction of fungi and their spores on inanimate surfaces. The present invention further provides for the use of such compositions in industrial and commercial processes or products to affect fungal resistant mediums such as textiles, leather, paper, coatings, paints, caulks, adhesives, sealants and surface contact cleaners for sanitizing surfaces for maximum residual results. The present invention also provides for the use of solubilized propionic acid or its solid salts with a dual cationic surfactant mixture to cause toxicity to fungi and its spores for immediate contact destruction with residual resistance on inanimate surfaces such as walls, floors, ceilings, countertops, and any exposed surface where fungal growth is present.

The present invention also provides for the use of solubilized propionic acid or its solid salts with a dual cationic surfactant mixture in the manufacture of animal hides, paper, wood, or other construction materials where increased resistance to fungal growths is desired. The present invention also discloses the use of solubilized propionic acid or its solid salts with a dual cationic surfactant mixture incorporated within paints and coatings to provide fungal resistance where said paints or coatings are applied; or, as an additive to impart fungal resistant properties in said paints or coatings by the consumer at times of application.

The present invention furthermore discloses the use of solubilized propionic acid or its solid salts with a dual cationic surfactant mixture with an incorporation of a cellulose ether, said incorporation to act as a thickener, emulsifier, cross-linker, or film-forming agent.

DETAILED DESCRIPTION OF THE INVENTION

The present invention utilizes propionic acid and/or salts thereof in compositions and methods of fungal inhibition and eradication. In certain embodiments of the present invention, the compositions and methods disclosed herein are directed toward imparting fungal resistance to construction materials. In certain such embodiments, a concentration of greater than 0.0% and less than 5.0% of calcium propionate (or the equivalent value of propionic acid) is in the compositions of the present invention. In still other embodiments of the compositions of the present invention, the concentration of propionic acid (or equivalent chemical value thereof) can range from 0.5% to 3.0%, or from 1.0% to 2.5%. The propionate compound concentrations described above are capable of providing a benign but effective fungicide as described herein.

In certain embodiments, the compositions of the present invention further include a dual cationic component. The dual cationic component of the present invention includes: wherein said quaternary ammonium compound ("quat") is selected from the group consisting of N-alkyldimethyl benzyl ammonium saccharinate; $1,3_55$-Triazine-1,3,5(2H,4H,6H)-triethanol; 1-Decanaminium, N-decyl-N,N-dimethyl-, chloride (or) Didecyl dimethyl ammonium chloride; 2-(2-(p-(Di-isobutyl)cresosxy) ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxyethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethylbenzyl ammonium chloride; alkyl dimethyl ethyl ammonium bromide (90% C14, 5% C16, 5% C12); alkyl dimemyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isopropylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldunethyl(ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) ocryl hydrogen ammonium chloride; dodecyl dimethyl benzyl ammonium, chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octylphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysilyl propyl dimethyl octadecyl ammonium chloride; trimethoxysilyl quats, and trimethyl dodecylbenzyl ammonium chloride.

In some of these embodiments, the dual cationic component is Maquat™ 2525 M 50% (Mason Chemical Company hereinafter "Maquat") at a concentration ranging from greater than 0.0% to 5% weight per weight. Maquat is comprised of two quaternary ammonium compounds in equal weight to total composition of matter. The two cationic surfactants in Maquat are alkyl dimethyl benzyl ammonium chloride and alkyl dimethyl ethyl benzyl ammonium chloride. Both of these cationic surfactants are known to possess limited antimicrobial effects and are classified as disinfectants.

Certain of these cationic components will readily mix with propionate compounds in solution. For example, 0.5% Maquat can be mixed with calcium propionate (at the concentrations listed above) to readily admix and provide a stable, clear solution.

Certain embodiments of the compositions of the present invention are made by adding Maquat to water at a concentration of 0.5% total weight. After thorough mixing, calcium propionate is introduced to the solution in the concentration of 2.5% by weight to the original water weight and thoroughly solubilized. The resultant composition is then ready for use as a surface disinfectant with relatively long residual effectiveness as a fungicide, bactericide, and viricide.

Dual quat blends, such as Maquat are known to be a highly effective disinfectant with numerous species of bacteria including *Enterococcus faecium, Escherichia coli, Escherichia coli* 0157:H7, *Pseudomonas aeruginosa, Salmonella cholerasuis, Salmonella typhi, Listeria monocytogenes, Staphylococcus aureus, Mycobacterium tuberculosis*, methicillin resistant *Staphylococcus aureus*, vancomycin intermediate resistant *Staphylococcus aureus*, and vancomycin resistant *Enterococcus faecalis*. The virucidal effectiveness of the quaternary compounds contained Maquat includes Hepatitis A, B, and C, HIV-1, Poliovirus Type 1, Canine Parvovirus, Norwalk virus, Human Coronavirus, and Rabies Virus. As a fungicide, an example is *Trichophyton mentagrophytes* (Athlete's foot fungus) (3M TB Quat Disinfectant Cleaner RTU Technical Data Brochure, September 2005).

To retard leaching and/or dilution of the solution upon application, a cellulose ether can be added to certain embodiments of the compositions of the present invention to aid in film-forming of the solution on a treated surface. Those of skill in the art will recognize that other film-forming agents can be utilized in the present invention, including, but not limited to, guar. In some embodiments, the cellulose ether can be sodium carboxymethylcellulose. The sodium carboxymethylcellulose concentrations in certain such embodiments can range from 0.05% to 0.5% weight per weight.

The compositions of the present invention can be applied by immersion of the material to be treated, by surface wiping, by brush, roller, pump spray applicator or pressure sprayer. The material can then be allowed to air dry the treated surfaces.

Suitable materials for treatment with the compositions and methods of the present invention include, but are not limited to, inanimate surfaces such as walls, floors, ceilings, countertops, and any exposed surface where fungal growth is present, as well as textiles, leather, paper, coatings, paints, caulks, adhesives, sealants and surface contact cleaners. Furthermore, certain compounds of the present invention, such as those containing solubilized propionic acid or its solid salts with a dual cationic surfactant mixture, can be incorporated within paints and coatings to provide fungal resistance where said paints or coatings are applied; or, as an additive to impart fungal resistant properties in said paints or coatings by the consumer at times of application.

Paper and textiles can furthermore be treated in pulp process and fiber process waters with the compounds of the present invention. In certain such embodiments, propionic acid or its solid salts can be solubilized at a concentration of greater than 0.0% and less than 5.0% in combination with a dual cationic component.

EXAMPLES

Propionic acid and its salts are inhibitors of some fungi with effectiveness for a period of approximately six days. In laboratory testing with a variety of methods and standards, each of the components when tested individually did not demonstrate resistance to various fungal species. However, as a combination in the concentrations described, immediate and sustained resistance to all fungi tested was demonstrated beyond the times as stipulated by the protocols of industry standards.

Example 1

Maquat 2525M 50%

A disk diffusion method of determining susceptibility of fungi to Maquat 2525M 50% was developed from the Kirby-Bauer Bactericidal Disk Diffusion Method. The diffusion method assumes the migration of active compounds into a surrounding agar medium (potato dextrose agar) to intercept and retard the growth of test inoculum seeded to the agar surface. This method was utilized as a screening method to achieve a rapid means of fungal inhibition after 5 days of incubation.

The inoculum was composed of a suspension of fungal spores harvested from one week cultures of ATCC #6205-*Chaetomium globosum*; ATCC #6275-*Aspergillus niger*; and, ATCC #10690-*Aspergillus terreus*. Once the plates were seeded with inoculum, DIFCO Concentration Disks (¼") were impregnated with a 0.5% solution of Maquat 2525M 50%, allowed to air dry in sterile petri dishes and placed at equidistant locations on each plate. At the end of the five day incubation at 30° C., 5 plates containing four disks each were examined visually and microscopically. No zones of inhibition manifested and on six of the twenty disks viable spores were observed. The specimens were graded as Moderately Resistant. Grading is based on the following scale: (1) not resistant—confluent growth and surface growth on disks; (2) moderately resistant—confluent growth without surface growth on disks; and (3) resistant—exhibits a zone of inhibition (no growth) surrounding disks with no surface growth or sporulation on disks.

Example 2

Calcium Propionate

Concurrent with the Maquat disk diffusion testing, exact methods were replicated for testing of calcium propionate. A 2.5% solution of calcium propionate was prepared and the DIFCO disks were impregnated with the solution, allowed to air dry and placed on the plates. At the end of the incubation period, the plates were examined visually and microscopically. All of the disks were occluded with profuse growth and were designated as No Resistance.

Example 3

Maquat 2525M 50% and Calcium Propionate

Concurrent with the above described testing, a solution of 0.5% Maquat and 2.5% calcium propionate was prepared and DIFCO disks were impregnated, allowed to air dry, and placed on the plates. After the incubation period, zones of inhibition were observed around all the disks measuring 12 mm. No growth was detected under microscopic examination. The plates demonstrated the exact effects for a period exceeding six weeks. The specimens were graded Fully Resistant.

Example 4

Maquat 2525M 50%, Calcium Propionate, and Sodium Carboxymethylcellulose

Concurrent with the above described tests, 0.5% of sodium carboxymethylcellulose was added to impart a solution with film forming properties and to determine if a cross linking agent would have any effects on the present invention. Examination of the incubated specimens was conducted and zones of inhibition of 10 mm manifested. No growth was present on any disks and an extended period of incubation exceeding six weeks presented no change in resistance or diminution of the zones of inhibition. The specimens were graded Fully Resistant.

Example 5

Cetylpyridinium Chloride and Calcium Propionate

Another cationic surfactant was selected to determine if calcium propionate exhibited the same synergistic, enhancing effects of resistance with fungi. A solution was created using 0.125% of cetylpyridinium chloride, equivalent to the concentrations of each of the components in Maquat 2525M 50%. Exact protocol was followed and examination of the specimen plates revealed no zone of inhibition surrounding the disks. The specimens were graded Moderately Resistant.

Example 6

TAPPI T 487 Calcium Propionate and Maquat 2525M 50%

Long term protection provided by a preservative mechanism to inhibit fungal growth is best demonstrated by the industry recognized TAPPI test method T 487. This method is used to determine the resistance of paper and paperboard to fungal growth in ideally suited controlled conditions of light, temperature, moisture, and food supply. Treated 50 mm test coupons of paper are placed on a surface of test agar, flooded with a test inoculum of fungal spores, and incubated to determine fungal resistance. The rating that is provided follows an established protocol to determine the degree of mold growth on a rating scale reported as 1) not fungal resistant; 2) moderately fungal resistant; and 3) resistant.

Challenges of treated porous surfaces, represented by selected samples of untreated paper product specified as Whatman filter paper #4 and paper product specified as Whatman filter paper #4 treated with a solution of fungicides, are exposed to designated fungal suspensions known to cause failure under certain use conditions. The test samples are prepared according to T 487 pm-99 by aseptically removing pre-sterilized 50 mm paper coupons, previously equilibrated to room temperature, and then placed in a controlled chamber at 28+/−1° C. (82.40 F) and 95%-98% RH. The chamber is fitted with a tray filled with a salt solution to maintain humidity control. The test ensues continuously for 21 days and samples are observed weekly. The panels are rated each week according to the appearance of fungal growth.

This series of tests according to the TAPPI T 487 pm-99 protocol were conducted with multiple specimens of treated and untreated (Control) paper substrates with the specified fungal species of *Aspergillus niger* (ATCC #6275), *Chaetomium globosum* (ATCC #6205), and *Aspergillus terreus* (ATCC #10690) suspensions. The suspensions of inoculum were harvested from 14 day potato dextrose agar cultures into sterile water, combining the culture suspensions from each fungal genus and adjusting to concentrations of $10^6$/ml. Triplicate substrate samples were then prepared from sheets of cellulose fiber papers (Whatman) cut into 50 mm squares and steam sterilized. The sterilized paper coupons were immersed in a solution of each challenge solution, allowed to soak for ten minutes, removed and placed into aluminum drying trays in a drying oven for 24 hours at 67° C. The test papers were placed onto the surface of prepared agar plates containing mineral-salt agar as outlined in T 487 pm-99. Two plies of paper were treated as a single test specimen and were directly pipetted with 1 ml of fungal suspension on the surface of each test coupon. The plates were then inverted and placed into humid incubation chambers and incubated at 28° C.+/−1 C for 21 days. Observations for growth were conducted on successive weekly schedules as well as verification of test inocula to distinguish contaminants or naturally occurring molds from actual challenge organisms. Growth was defined as sporulating, hyphael appearances directly from the paper substrate. The following comparative table depicts the various solutions and resistance results:

TABLE 1

| Solution | Days in Incubation | Resistance Grade |
| --- | --- | --- |
| 2.5% calcium propionate; 0.5% Maquat 2525M 50% | N/A | Resistant |

TABLE 1-continued

| Solution | Days in Incubation | Resistance Grade |
| --- | --- | --- |
| Calcium propionate 2.5% | 8 | Not resistant |
| Maquat 0.5% | 16 | Not resistant |
| 2.5% calcium propionate; 0.5% Maquat 2525M 50%; sodium carboxymethylcellulose 0.5% | N/A | Resistant |
| 1.5% propionic acid | 9 | Not resistant |
| 1.25% cetylpyridinium chloride | 15 | Not resistant |
| Thiabendazole (TBZ) 1.0% Merck AgVet | 17 | Moderately resistant |
| Amical Flowable 0.75% Dow Agro | 16 | Moderately resistant |

What is claimed:

1. An antifungal composition comprising:
   (a) 2.5% calcium propionate; and
   (b) 0.5% of a dual cationic composition comprising 25% alkyl dimethyl benzyl ammonium chloride and 25% alkyl dimethyl ethyl benzyl ammonium chloride.

2. The antifungal composition of claim 1, further comprising a film-forming agent.

3. The antifungal composition of claim 2, wherein the film-forming agent is cellulose ether.

4. The antifungal solution of claim 1 further comprising a film-forming agent and a liquid component.

5. The antifungal composition of claim 4, wherein the film-forming agent is cellulose ether.

6. An inanimate object or material treated with the antifungal composition of claim 1, wherein the object or material is selected from the group consisting of textiles, leather, paper, coatings, paints, caulks, adhesives, sealants and surface contact cleaners, animal hides, wood, and construction materials.

7. A method of using the antifungal composition of claim 1 comprising treating a material or object with the antifungal compound, wherein the material or object is selected from the group consisting of textiles, leather, paper, coatings, paints, caulks, adhesives, sealants and surface contact cleaners, animal hides, wood, and construction materials.

8. The method of claim 7, comprising coating the surface of the material or object to be treated in the antifungal compound.

9. The method of claim 7, comprising applying the antifungal compound to a surface of the material or object to be treated by brush, roller, pump spray applicator or pressure sprayer.

10. The method of claim 9 further comprising allowing the material or object to be treated to air dry.

11. The method of claim 7, comprising adding the antifungal compound or solution to a paint or coating prior to application of the paint or coating.

12. The method of claim 7, comprising immersing the material or object to be treated in the antifungal compound.

* * * * *